United States Patent [19]

Galasso

[11] Patent Number: 5,419,341
[45] Date of Patent: May 30, 1995

[54] COMPLEMENTARY PRODUCT FOR A CONDOM HAVING A CLOSURE FLAP

[76] Inventor: Raymond M. Galasso, 1969 Woodland, Sylvan Lake, Mich. 48320

[21] Appl. No.: 183,167

[22] Filed: Jan. 18, 1994

[51] Int. Cl.[6] .............................................. A61F 6/04
[52] U.S. Cl. ..................................... 128/844; 604/349; 128/918
[58] Field of Search ............... 128/843, 844, 918, 842, 128/843, 844, 918; 604/346–353

[56] References Cited

U.S. PATENT DOCUMENTS

| | | | |
|---|---|---|---|
| 2,365,556 | 12/1944 | Karg | 128/844 |
| 4,588,397 | 5/1986 | Giacalone | 604/349 |
| 4,888,007 | 12/1989 | Loeb et al. | 128/844 |
| 4,898,184 | 2/1990 | Skurkovich et al. | 128/844 |
| 4,955,392 | 9/1990 | Sorkin | 128/844 |
| 5,111,831 | 5/1992 | Foggia | 128/842 |
| 5,163,449 | 11/1992 | Valk | 128/918 |
| 5,176,152 | 1/1993 | Wheeler | 128/844 |
| 5,275,177 | 1/1994 | Wilk | 128/849 |

Primary Examiner—Jerome L. Kruter
Attorney, Agent, or Firm—Raymond M. Galasso

[57] ABSTRACT

An apparatus (10,110,210) for facilitating the removal of a condom (12,112,212) from a penis (14,114,214) and for preventing the entanglement of the condom (12,112,212) with pubic hair (16,116,216) located on the penis (14,114,214) and on the pubic area (18,118,218) adjacent the penis (14,114,214). The apparatus (10,110,210) comprises an elongated tubular sleeve (24,124,224) having a first open end (26,126,226), a second open end (28,128,228) and a flange (20,120,220) extending radially outwardly from the first open end (26,126,226).

1 Claim, 2 Drawing Sheets

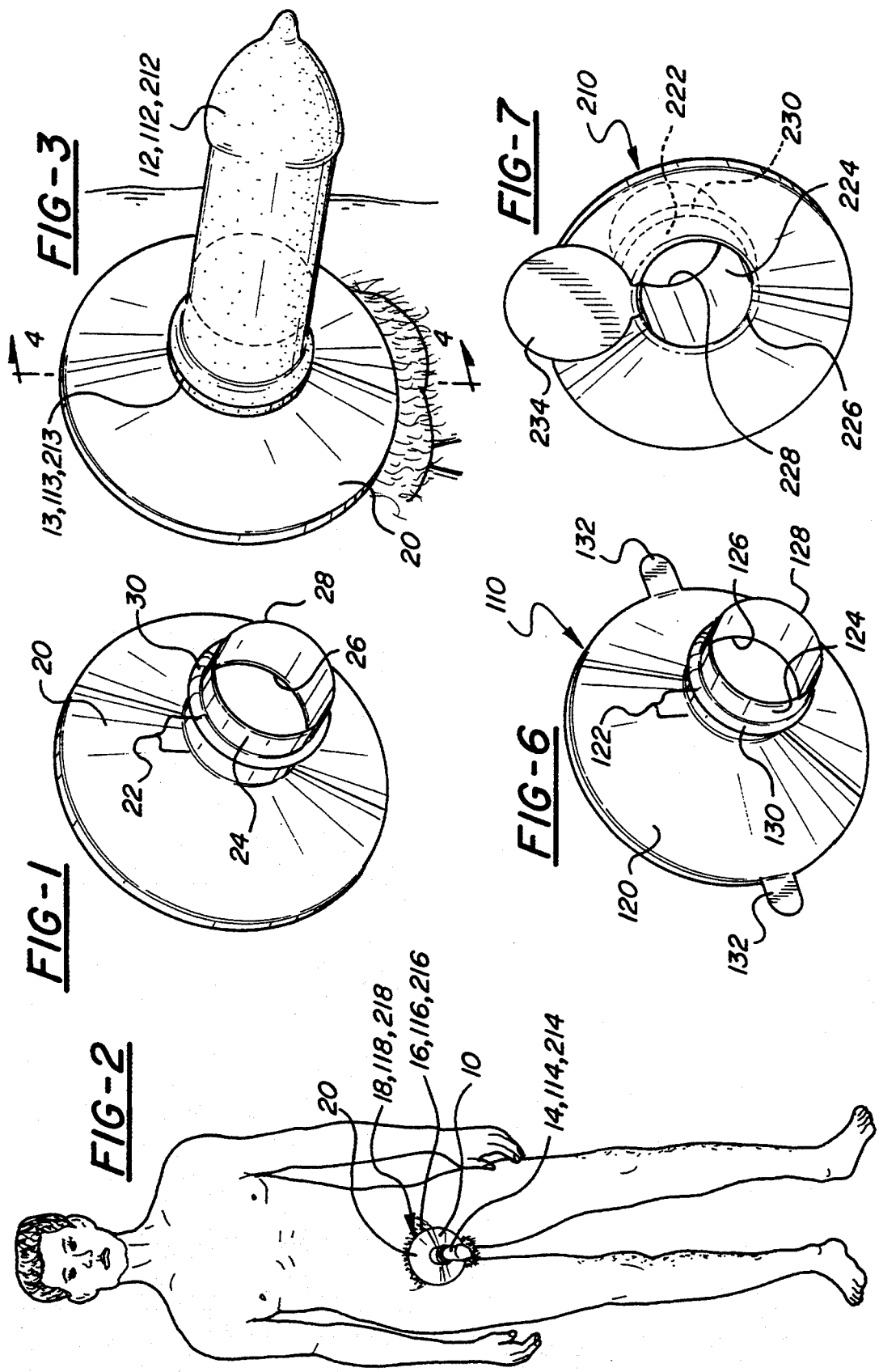

COMPLEMENTARY PRODUCT FOR A CONDOM HAVING A CLOSURE FLAP

TECHNICAL FIELD

This invention, in general, relates to apparatuses for removing a condom after use. Specifically, this invention relates to an apparatus for facilitating the removal of a condom from a penis and for preventing the entanglement of the condom with pubic hair located on the penis and on the pubic area adjacent the penis.

BACKGROUND OF THE INVENTION

Since their introduction, the design of rolled condoms have remained the same. Rolled condoms have been proven by the consuming public and manufacturers to be superior to unrolled condoms due to the ease in which they are applied to an erect penis and the ability to compactly package them.

However, there are several problems that have persistently arisen with this traditional design. These problems have caused many consumers in the contraceptive market to find alternative contraceptive products. The first problem is the discomfort caused from the rolled portion of the condom. The rolled portion causes two types of pain. The first pain is caused by the pressure exerted against the skin at the base of the penis. The second pain is caused by the entanglement of the user's pubic hair with the rolled portion either during copulation due to the condom's slippage or when the user attempts to remove the condom.

The second problem with the traditional design is slippage of the condom during sexual activity. During copulation, sexual fluids are released which reduce friction between the condom and the penis and therefore increase slippage.

The third problem with the traditional design is the need for the user to grab the condom to remove it after copulation. This requires the user to touch the sexual fluids released during copulation. This less than sanitary means for removing the condom after use is unpleasant for the user but more importantly increases the chances for contracting sexually transmitted diseases such as syphilis, gonorrhea, chlamydial infections, genital herpes simplex virus (HVS) infections, genital human papillomavirus (HPV) infections, hepatitis A infection, hepatitis B infection, cytomegalovirus infections, acquired immunodeficiency syndrome (AIDS).

The traditional rolled condom also does not provide protection to the pubic area surrounding the penis from sexually transmitted diseases. Finally, the traditional design does not leave the user with an indiscrete but effective means for disposing of the condom.

Despite the problems discussed above, the traditional rolled condom designs still provide an excellent means for preventing conception and sexually transmitted diseases. Also, the rolled condom product, in its present form, is still a consumer success. Instead of redesigning the basic rolled condom product, a new product complementary to the present rolled condom designs is needed to alleviate its problems set out above.

SUMMARY OF THE INVENTION

In view of the above mentioned problems with the traditional condom design and the need for a complementary product that alleviates these problems, an apparatus for facilitating the removal of a condom from a penis and for preventing the entanglement of the condom with pubic hair located on the penis and on the pubic area adjacent the penis is provided. The apparatus comprises an elongated tubular sleeve adapted to cover a portion of the penis so that the sleeve lies between the penis and the condom covering the penis. The sleeve has a first open end and a second open end. The apparatus is characterized by a flange extending radially outwardly from the first open end for preventing entanglement of the condom with the pubic hair located on the pubic area adjacent the penis and for facilitating the removal of the condom from the penis.

It is a primary object of the present invention to provide a means for preventing the entanglement of pubic hair with a condom without modifying the present condom designs.

A secondary object of the present invention is to provide the user the ability to remove a condom without having to touch it.

An additional object of the present invention is to prevent slippage of the condom during sexual activity.

A further object of the present invention is to prevent the transmission of sexually transmitted diseases.

Another advantage of the present invention is to prevent the pain caused by the pressure exerted by the unrolled portion of the condom against the penis.

Yet another advantage of the present invention is to provide the user with the ability to dispose of a condom in a sanitary and indiscrete manner.

FIGURES IN THE DRAWINGS

Other advantages of the present invention will be readily appreciated as the same becomes better understood by reference to the following detailed description when considered in connection with the accompanying drawings wherein:

FIG. 1 illustrates the preferred embodiment of the present invention prior to use.

FIG. 2 illustrates the preferred embodiment of the present invention on a user's body prior to rolling on a condom.

FIG. 3 illustrates the preferred embodiment of the present invention on a user's body with a condom rolled in place.

FIG. 6 illustrates a second embodiment of the present invention.

FIG. 7 illustrates a third embodiment of the present invention.

DESCRIPTION OF THE PREFERRED EMBODIMENT

Figure 4:
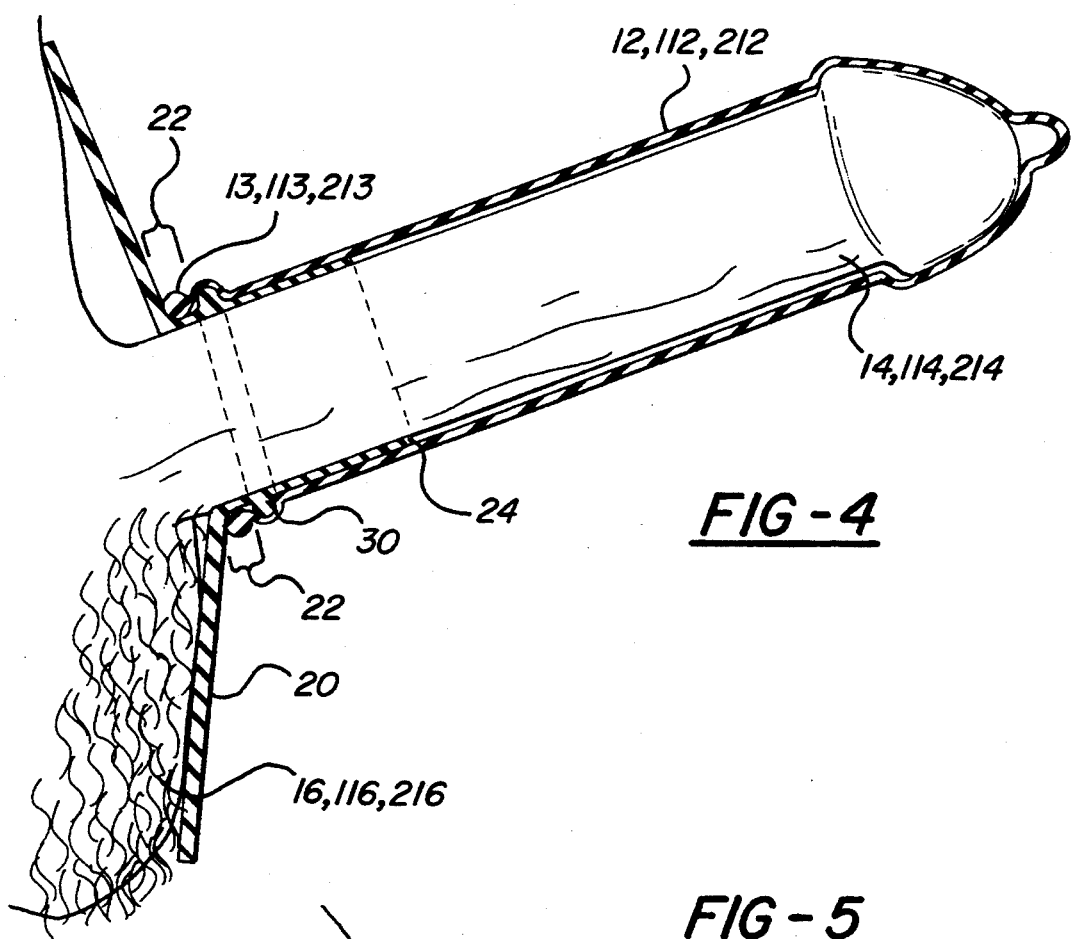
FIG. 4 illustrates a cross sectional view (taken about line 4—4 of FIG. 3) of the preferred embodiment of the present invention on a user's body with a condom rolled in place.

Referring to FIGS. 1 and 2, the apparatus of the present invention is generally indicated by the reference numeral 10. The apparatus 10 is designed to facilitate the removal of a condom 12 of the type having an unrolled portion 13 from a penis 14 and for preventing the entanglement of the condom 12 with pubic hair 16 located on the penis 14 and on the pubic area 18 adjacent the penis 14. The apparatus 10 comprises an elongated tubular sleeve 24 adapted to cover a portion of the penis 14 so that said sleeve 24 lies between the penis 14 and the condom 12 covering the penis 14 as shown best in FIGS. 3 and 4. The sleeve 24 has a first open end 26 and a second open end 28.

According to the present invention, the apparatus 10 comprises a flange 20 extending radially outwardly from said first open end 26 for preventing entanglement of the condom 12 with the pubic hair 16 located on the pubic area 18 adjacent the penis 14 and for facilitating the removal of the condom 12 from the penis 14. In other words, the flange 20 primarily acts as both a barrier between the unrolled portion 13 of the condom 12 and the pubic hair 16 located on the pubic area 18 and a handle for the user to easily grab. In the preferred embodiment, the apparatus 10 is constructed from a latex material. The flange 20 must be of sufficient thickness to provide the flange 20 with sufficient rigidity so that the flange 20 remains flush with the user's body during copulation or other sexual activity. In the preferred embodiment, the flange 20 is also conically shaped to aid in keeping the flange 20 flush with the user's body. However, the flange 20 can have any shape and size as long as the flange 20 keeps the unrolled portion 13 away from the pubic hair 16. The apparatus 10 can also be constructed of either a rubber or plastic material. The apparatus 10 includes a retaining means or rib 30 for retaining the condom 12 on the tubular sleeve 24 to prevent the inadvertent separation of the condom 12 from the apparatus 10. The rib 30 extends outwardly from the tubular sleeve 24. Once the condom 12 is rolled over the sleeve 24, the unrolled portion 13 is rolled into a groove 22 located between the flange 20 and rib 30. Thus, the unrolled portion 13 is wedged between the flange 20 and rib 30 and prevents the inadvertent detachment of the condom 12 from the apparatus 10 during copulation or after copulation when the apparatus 10 is used to remove the condom 12 from the penis 14. In this manner, slippage of the condom 12 is prevented. Although the retaining means is shown and described to include the one rib 30—groove 22—flange 20 combination, any other suitable means for retaining the condom 12 to the apparatus 10 may be employed and the same is considered to be a part of the present invention. For example, more the one rib 30 may be used to retain the condom 12 to the apparatus 10.

FIG. 6 illustrates a second embodiment of the present invention. The apparatus 100 of this embodiment is identical to the preferred embodiment 10 except for a tab member 132 extending from the flange 120 for pulling the apparatus 100 and condom 112 off the penis 114.

FIG. 7 illustrates a third embodiment of the present invention. The apparatus 200 of this embodiment is identical to the preferred embodiment 10 except for a flap 234 attached to the flange 220 for covering the first open end 226 of the tubular sleeve 224. With flap 234, the apparatus 200 can be used as a disposal bag for the condom 212 after use. After removing the apparatus 200 and condom 212 from the penis 214, the user secures the flap 234 to the flange 220 to cover the first open end 226. The flap 234 is secured to the flange 220 by conventional means such as by a peel and stick feature, i.e., an adhesive is applied to one side of the flap 234 and covered by coated paper which is peeled away to expose the adhesive upon use. The flap 234 prevents the sexual juices contained within the condom 212 from leaking from the first open end 226.

Figure 5:
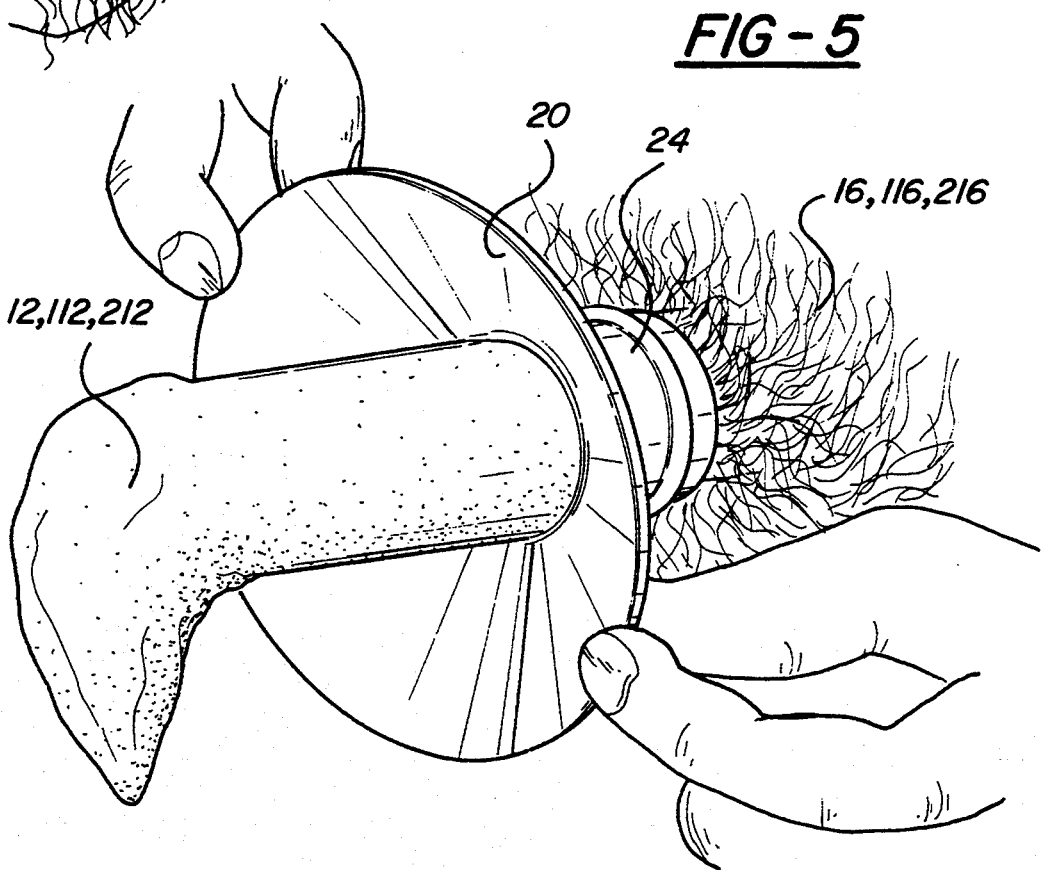
FIG. 5 illustrates the removal of a condom by a user of the preferred embodiment.

The apparatus 10,100,200 is applied to the user's body prior to applying the condom 12,112,212. First, the user places his penis 14,114,214 through the first open end 26,126,226. Next, the apparatus 10,110,210 is pulled toward the pubic area 18,118,218 until the flange 20,120,220 abuts the pubic area 18,118,218 so that a portion of the penis 14,114,214 extends beyond the second open end 28,128,228 (See FIG. 2). The user then rolls the condom 12,112,212 on his penis 14,114,214 and over the tubular sleeve 24,124,224 until the unrolled portion 13,113,213 sits in groove 22,122,222 between the rib 30,130,230 and flange 20,120,220 (See FIGS. 3 and 4). After sexual activity is completed, the user either grabs the flange 20,120,220 or tab member 132 and pulls the apparatus 10,100,200 away from the pubic area 18,118,218 so that the condom 12,112,212 slides off the penis 14,114,214 (See FIG. 5). In this manner, the user does not have to touch the condom 12,112,212 after applying it to his penis 14,114,214. Thus, the user never has to come into contact with the sexual juices on the condom 12,112,212 after its use. The tight fit of the condom 12,112,212 against the tubular sleeve 24,124,224 and penis 14,114,214 keeps the apparatus 10,100,200 attached to the condom 12,112,212 thus allowing the condom 12,112,212 to be removed by the apparatus 10,100,200. After removing the apparatus 10,100,200 and condom 12,112,212 from the penis 14,114,214, the apparatus 10,110,210 can be wrapped around the condom 12,112,212. In this manner, the apparatus 10,110,210 can be used to dispose of the condom 12,112,212 without having to ever touch it. In one embodiment of the present invention, the flap 234 can be used to cover the first open end 226 of the sleeve 224 so that the sexual fluids contained in the condom 212 do not leak from the apparatus 210 when the apparatus 210 is being used as a disposal bag for the condom 212.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims wherein reference numerals are merely for convenience and are not to be in any way limiting, the invention may be practiced otherwise than as specifically described.

We claim:

1. An apparatus (10,110,210) for facilitating the removal of a condom (12,112,212) from a penis (14,114,214) and for preventing the entanglement of the condom (12,112,212) with pubic hair (16,116,216) located on the penis (14,114,214) and on the pubic area (18,118,218) adjacent the penis; said apparatus (10,110,210) comprising:

an elongated tubular sleeve (24,124,224) adapted to cover a portion of the penis (14,114,214) so that said sleeve (24,124,224) lies between the penis (14,114,214) and the condom (12,112,212) covering the penis (14,114,214), said tubular sleeve (24,124,224) having a first open end (26,126,226) and a second open end (28,128,228);

a conically shaped flange (20,120,220) extending radially outwardly from said first open end (26,126,226) for preventing entanglement of the condom (12,112,212) with the pubic hair (16,116,216) located on the pubic area (18,118,218) adjacent the penis (14,114,214) and for facilitating the removal of the condom (12,112,212) from the penis (14,114,214); and said flange (220) having a flap (234) for covering said first open end (226).

* * * * *